United States Patent [19]
Curéet al.

[11] Patent Number: 5,792,329
[45] Date of Patent: Aug. 11, 1998

[54] APPARATUS TO MEASURE AN ELECTRO-CHEMICAL ACTIVITY

[75] Inventors: Omer Paul Ivo Curé, Diepenbeek; Guido Jacobus Neyens, Maaseik/Opoeteren, both of Belgium

[73] Assignee: Heraeus Electro-Nite International, N.V., Houthalen, Belgium

[21] Appl. No.: 727,460

[22] PCT Filed: Mar. 6, 1996

[86] PCT No.: PCT/EP96/00952

§ 371 Date: Oct. 18, 1996

§ 102(e) Date: Oct. 18, 1996

[87] PCT Pub. No.: WO96/32636

PCT Pub. Date: Oct. 17, 1996

[30]   Foreign Application Priority Data

Apr. 12, 1995 [DE] Germany ................ 195 13 212.2
Aug. 29, 1995 [DE] Germany ................ 195 31 661.4

[51] Int. Cl.⁶ ............ G01N 27/406; G01N 27/411
[52] U.S. Cl. ............ 204/423; 204/422; 205/784
[58] Field of Search ............ 204/421–429; 205/783.5, 784, 784.5, 785

[56]   References Cited

U.S. PATENT DOCUMENTS

| | | | |
|---|---|---|---|
| 3,468,780 | 9/1969 | Fischer | 204/422 |
| 3,578,578 | 5/1971 | Von Krusenstierna | 204/422 |
| 3,616,407 | 10/1971 | Engell et al. | 204/423 |
| 5,342,489 | 8/1994 | Iwase et al. | 204/422 |

FOREIGN PATENT DOCUMENTS

| | | |
|---|---|---|
| 0 108 431 B1 | 5/1984 | European Pat. Off. . |
| 0 148 492 A1 | 7/1985 | European Pat. Off. . |
| 0 208 072 A1 | 1/1987 | European Pat. Off. . |
| 0 450 090 A1 | 10/1991 | European Pat. Off. . |
| 3446320 C1 | 2/1986 | Germany . |
| 58-223742 A | 12/1983 | Japan . |

OTHER PUBLICATIONS

B. Korousic, "Application of Oxygen Sensor for Measurement of the Oxygen Potential in the Matter ESR–Slags," *Radex–Rundschau* vol. 1, pp. 236–243 (May 1990).

*Primary Examiner*—T. Tung
*Attorney, Agent, or Firm*—Panitch Schwarze Jacobs & Nadel, P.C.

[57]   ABSTRACT

The invention relates to a method to measure an electro-chemical activity of a non-metallic liquid layer lying on a molten bath by means of a measuring cell with an electro-chemical element which has an active part and with a counter electrode. The invention also relates to a measuring cell to measure an electro-chemical activity. In order to achieve exact measuring results of an electro-chemical activity with the least possible expenditure, the measuring cell is dipped through a non-metallic liquid layer into a molten bath, the active part of the electro-chemical element being surrounded by the non-metallic liquid layer of the material of this layer on insertion, this material being held at the electro-chemical element until after measuring the electro-chemical activity and the measurement being carried out after dipping the electro-chemical element into the molten metal within the molten bath. The electro-chemical element is especially developed to enable that the material to be measured adheres to it.

8 Claims, 5 Drawing Sheets

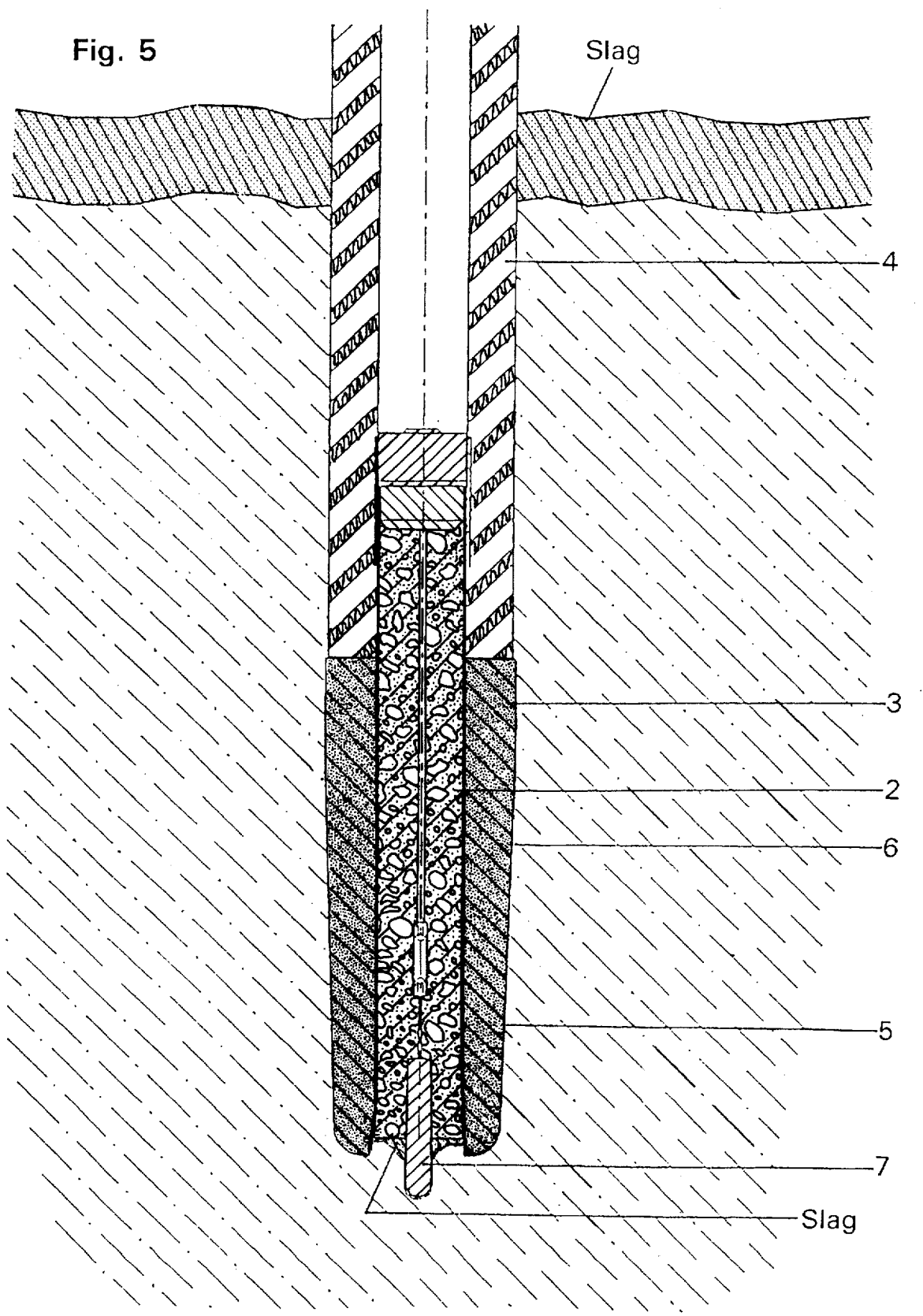

5,792,329

APPARATUS TO MEASURE AN ELECTRO-CHEMICAL ACTIVITY

BACKGROUND OF THE INVENTION

This invention relates to a method to measure an electro-chemical activity of a non-metallic liquid layer lying on a molten bath by means of a measuring cell with an electro-chemical element which shows an active part and with a counter electrode. Furthermore, this invention relates to a measuring cell to measure an electro-chemical activity.

It is often necessary to not only carry out measurements in molten baths but also to carry out measurements in layers lying above the molten baths. It is for example necessary for the evaluation of the course of metallurgic processes when producing steel to measure the oxygen potential of slag. It may also be necessary to measure activities in cryolite meltings during the aluminium electrolysis in order to be able to monitor and control the metallurgic process.

It is known from Radexrundschau 1990, pages 236 to 243, to carry out oxygen measurements directly in slag. Here, an ordinary electro-chemical sensor is arranged in the slag. The electro-chemical sensor is equipped with a measuring cell with a counter electrode and an electro-chemical element. The electro-chemical element is formed in the known way out of a reference electrode which is arranged in a reference material. This reference material is again surrounded by a small solid-electrolyte tube. Such measuring cells are, for example, also known from EP 0 108 431. They are used for the measurement of oxygen activities in molten baths with the measuring cell itself being protected while passing through the layer lying above it (for example slag) by a protecting cap.

The known direct measurements of oxygen activities in melted layers arranged above a molten bath, like slag or cryolite, demand the exact placing of the electro-chemical element within the layer to be measured. This layer is normally relatively thin (e.g. for ladle slag approximately 0 to 15 cm) so that diverging placements of the electro-chemical element normally also entail diverging measurement results. The exact arrangement of the measuring cell therefore often demands a relatively high expenditure of energy and cost as the level of surface of the molten bath cannot be easily determined. The positioning therefore demands a relatively long dipping time of the probe so that for example the counter electrode and the measurement leads can get damaged.

Moreover, methods to analyze slags are known in which the slag samples are taken and analyze after their solidification and partly after remelting.

SUMMARY OF THE INVENTION

Proceeding from the known state of art, the invention is based on the task to provide a method to measure an electro-chemical activity which supplies exact measuring results with the least possible expenditure. Furthermore, it is the task of this invention to provide a suitable electro-chemical element as well as a measuring cell for these measurements.

According to the invention the task for the above characterized method is solved in that the measuring cell is dipped through the non-metallic liquid layer into the molten bath, in that the active part of the electro-chemical element is while passing through the non-metallic liquid layer surrounded by the material of this layer, in that this material is kept at the electro-chemical element until after the measurement of the electro-chemical activity and in that the measurement is carried out in the molten metal after dipping the electro-chemical element into the molten metal within the molten bath. A measuring cell is understood to be an arrangement of at least one electro-chemical element and a counter electrode, the counter electrode being arranged immediately next to the electro-chemical element or distant from it. The counter electrode can for example be fixed at the wall of the melting container or be a part of this wall. In this case, of course, the counter electrode is naturally not dipped through the non-metallic liquid layer into the molten bath. With this method the measurements are carried out in an almost constant surrounding. An exact placing of the measuring cell is not necessary as the molten bath normally has a sufficient height. The temperature distribution within the molten bath is substantially more homogeneous than in the layer lying on it which activity is to be measured so that the influence of temperature fluctuation on the measuring result is negligible against the known direct measuring method. The measurements are carried out under almost constant surrounding conditions so that reproducible and/or comparable measuring results can be obtained.

To increase the exactness and the reproducibility of measurements it has proven advantageous that while passing the insertion end of the measuring cell through the non-metallic liquid layer the counter electrode is not fully surrounded by the material of this layer and/or that this material is removed at least partly from the counter electrode before measuring so that the counter electrode has direct contact with the molten bath. This can for example happen while remelting. It can be advantageous to determine the oxygen activity of the material to be measured. This material which is a non-metallic liquid layer lying on a molten bath can for example be slag for iron meltings or cryolite for aluminium electrolysis.

The task for a measuring cell to measure an electro-chemical activity of a non-metallic liquid layer on a molten bath with an electro-chemical element arranged at a holder which has a small solid-electrolyte tube with an active part and a counter electrode is solved in that the electro-chemical element and the counter electrode are arranged in the molten bath with the active part being surrounded by the material of the non-metallic layer to be measured and at least one part of the counter electrode having direct contact with the molten bath that is, that it is not completely surrounded by the non-metallic layer of the material to be measured. The direct contact of the counter electrode with the molten bath produces particularly exact measuring results. It has proven advantageous for exact measuring results that the active part is formed as a ring-shaped surface area of the electro-chemical element. The counter electrode can be protected by a coating, for example cardboard, before being used. This protection coating is destroyed when passing through the layer to be measured or in the molten bath and prevents that the material of the layer to be measured adhering to the counter electrode.

It is convenient that the insertion end of the small solid-electrolyte tube is coated with an electrically insulating material, the area between the insertion end and the fireproof body not being coated. For example $Al_2O_3$ or $MgO$ have proven to be especially suitable coating materials. Such a coating insures that the material of the layer to be measured adheres to the electro-chemical element so that the activity measurement can be carried out in the molten bath lying below it. Naturally, the material of the layer to be measured can adhere to the small solid-electrolyte tube in different ways, for example by a suitable mechanical collecting facility for this material in the form of a tube surrounding the electro-chemical element at a certain distance.

It is convenient that the insertion end is maximally 6 mm coated in the direction of the fire-proof body, especially that the coating is approximately 2.5 mm long. It has furthermore proven advantageous that the electro-chemical element projects out of the fire-proof body by approximately 9 to 13 mm, especially approximately 11 mm. Such a dimensioning insures good adherence to the electro-chemical element of the material to be measured and also a reliable measurement of the activity of this material. It can furthermore be convenient that a thermoelement is arranged in the electro-chemical element as the electro-chemical activity is also temperature dependent and with this the influence of possible temperature fluctuations can be considered.

The task for a dipping measuring sensor to measure an electro-chemical activity of a non-metallic liquid layer lying on a molten bath with an electro-chemical element arranged at a holder and a counter element is solved in that a protection layer of non-fire-proof material is arranged on the counter electrode while dipping into the non-metallic liquid layer and that the electro-chemical element has no protection layer while dipping into the non-metallic liquid layer. The protection layer of the counter electrode prevents the counter electrode from being covered by slag as it passes through the slag layer. The protection layer dissolves in the molten bath lying below it, it burns or melts for example. In addition to cardboard other materials can be used, for example a metal layer as copper which has a low melting point. While the counter electrode is not covered by slag, the slag can adhere to the surface of the electro-chemical element and is inserted into the molten bath as the slag can get to the electro-chemical element directly due to the lack of a protection cap or of a similar direct way. It is possible to protect the electro-chemical element with a protection layer or a protection cap, e.g. cardboard, against mechanical damage during transport, etc.. The protection cap is removed before use of the dipping measuring sensor or it burns due to the radiant heat before insertion.

It has proven advantageous that the protection layer is formed out of cardboard and that the whole surface of the counter electrode is preferably covered by the protection layer at the outside of the holder. It is furthermore convenient that the electro-chemical element projects approximately 9 to 13 mm out of the holder. In an advantageous embodiment of the dipping measuring sensor the holder has a cardboard tube at which insertion end a measuring head out of fire-proof material is arranged, the counter electrode surrounding the electro-chemical element at least partly in a ring shape, for example, in that it is led through the measuring head as a metal tube and it is projecting out of it at its front. It is furthermore convenient that the contacts of the counter electrode and the contacts of the electro-chemical element are inside the holder. These contacts are connected to a measuring and evaluation electronics in the known method.

The invention is according to this solved in that a measuring cell with an electro-chemical element arranged in a holder is used and with a counter electrode to carry out measurements of the electro-chemical activity of the material in a molten bath in a non-metallic liquid layer lying on the molten bath.

BRIEF DESCRIPTION OF THE SEVERAL VIEWS OF THE DRAWING

An embodiment of the invention is described in detail by means of the following drawing. The drawing shows in:

FIG. 5 a measuring element inserted into a melting container where slag adheres to the electro-chemical element and the counter electrode is partly melted off and partly covered by slag.

DETAILED DESCRIPTION OF THE INVENTION

Figure 1:
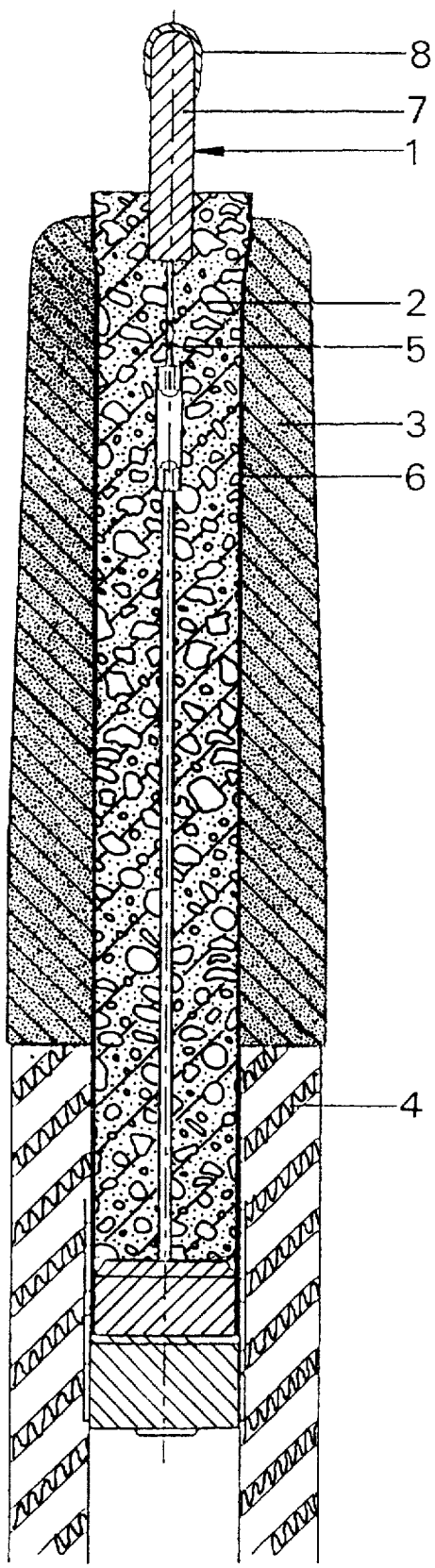
FIG. 1 an exemplary embodiment of a measuring cell with an electro-chemical element according to the invention.

The measuring cell has according to FIG. 1 an electro-chemical element which is arranged with cement 2 in a holder. The holder made is made out of fire-proof material 3 at the insertion end of the measuring cell, for example moulding sand, and, in connection with it, formed out of a cardboard tube 4. An electrode 5 projects out of the electro-chemical element 1 which is connected to the measuring electronics. The counter electrode 6 is formed out of a metal tube which surrounds the electrode 5 and projects out of the fire-proof material 3 of the holder at the insertion end of the measuring cell. This projecting part is surrounded by a layer of cardboard which is not shown in the drawing and which is to prevent that material from adhering while the insertion end of the measuring cell penetrates the non-metallic liquid layer lying on a molten bath. The small solid-electrolyte tube 7 of the electro-chemical element 1 is coated with an electrical insulating material 8 at its insertion end. This layer is substantially made out of MgO, it can, however, also be out of $Al_2O_3$ or another insulating material. The layer is approximately 50 mm thick; it can also be a little bit thicker. The coating is approximately 2.5 mm long in direction to the fire-proof body. Between the area where the electrical insulated material 8 is arranged on the small solid-electrolyte tube and the fire-proof material in which the small solid-electrolyte tube 7 is embedded, there is an approximately 11 mm long uncoated area, the so-called active part of the electro-chemical element 1.

For measurement the measuring cell is inserted into the slag layer lying on a steel melting. Here, the electro-chemical element 1 is surrounded by slag so that slag is also inserted into the steel melting. The temperature balance is quickly reached in the steel melting in the area of the electro-chemical element 1 and the oxygen activity of the liquid slag layer is measured. The cardboard 10 which is arranged at the counter electrode 6 prevents slag from adhering adheres to the counter electrode 6 while passing through the slag layer. In doing this, the counter electrode 6 is in direct contact with the steel melting while measuring.

Figure 2:
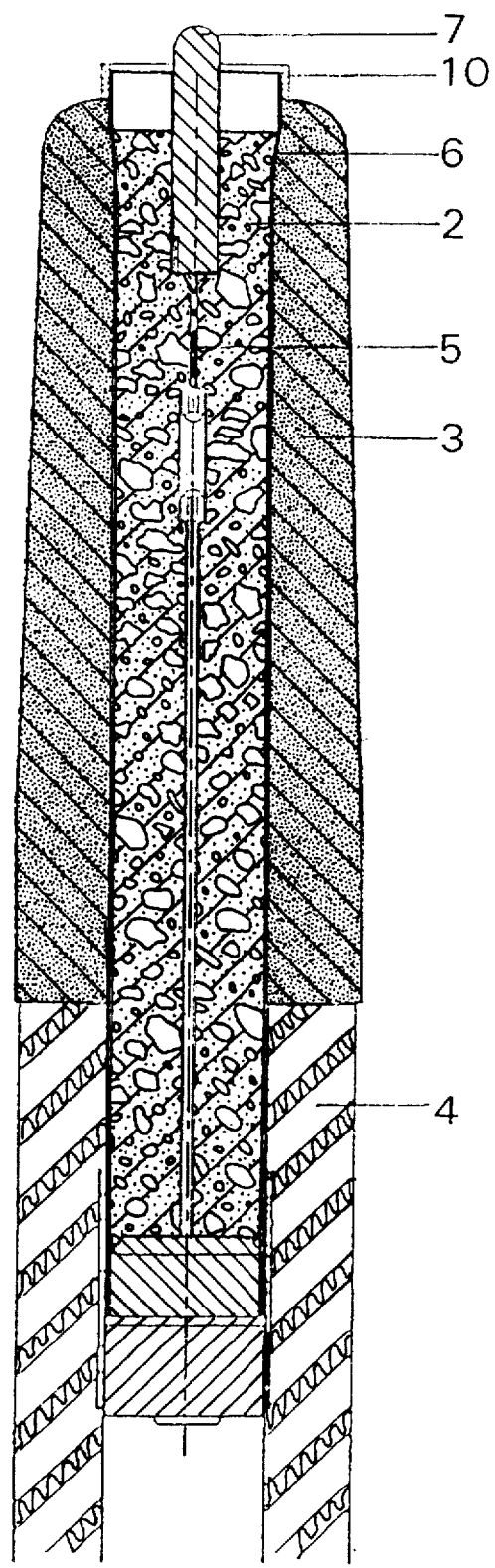
FIG. 2 an embodiment with an uncoated small electrolyte tube (diameter 5 mm)
Figure 3:
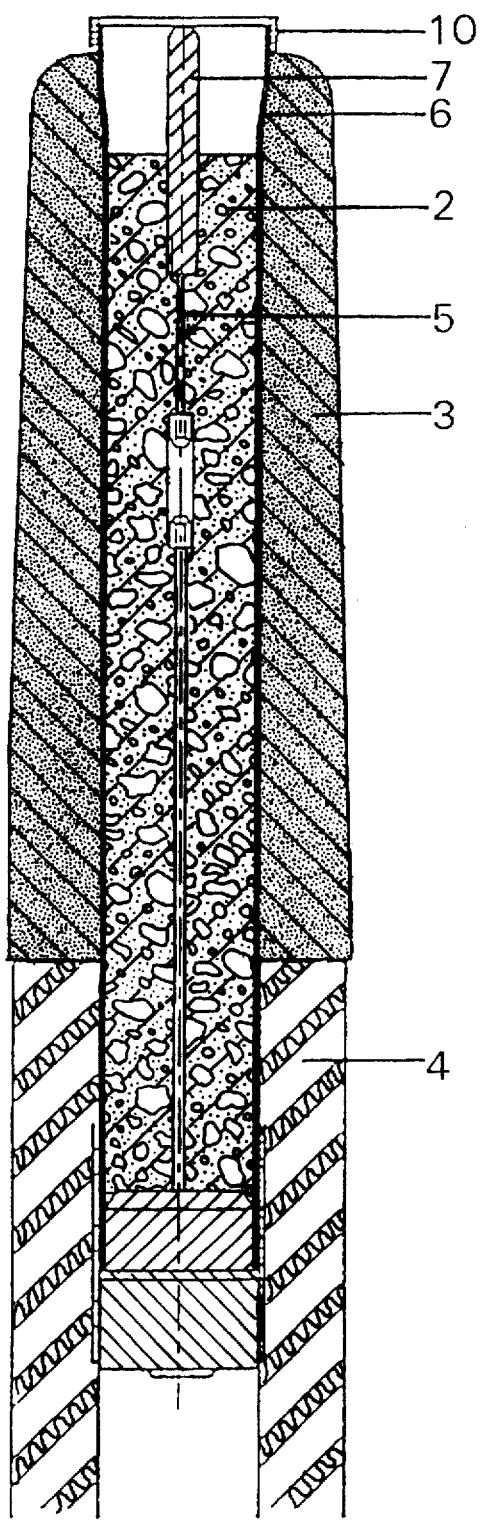
FIG. 3 an embodiment with an uncoated thin small electrolyte tube (diameter 3 mm), where the small tube does not project out of the counter electrode.
Figure 4:
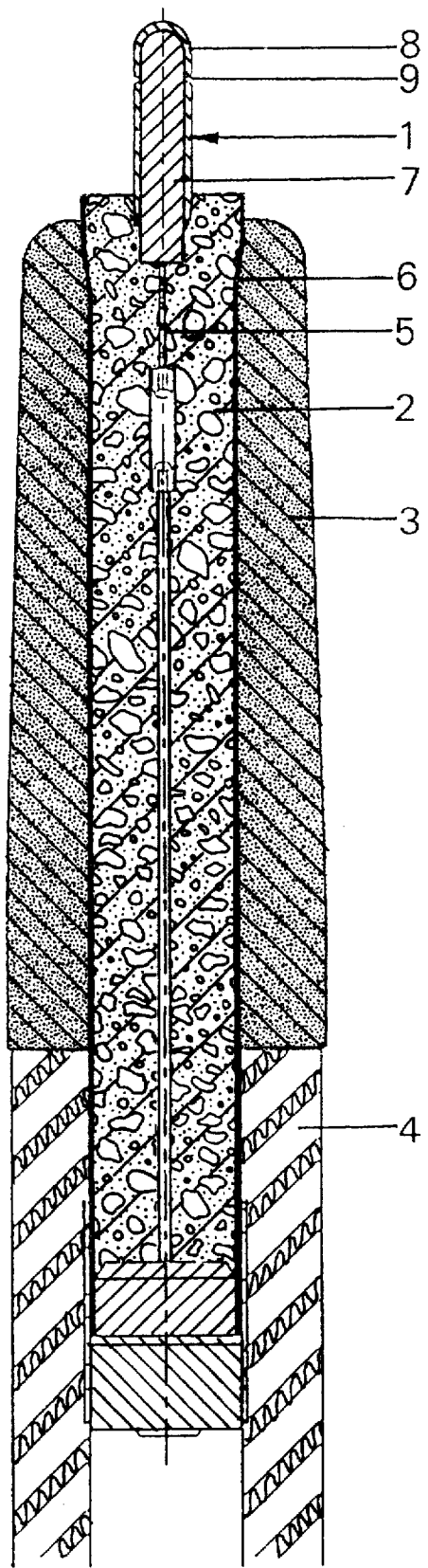
FIG. 4 an embodiment in which the active part is a ring-shaped surface area of the electro-chemical element.

Instead of the electrical insulating material 8 at the top of the electro-chemical element 1 other materials can also be used which cause the slag to adhere to the electro-chemical element 1. The electro-chemical element 1, which projects approximately 9 to 13 mm, especially 11 mm, out of the cement 2, could for example be surrounded by a small tube, for example the counter electrode 6 protected by cardboard 10, while building a ring area as shown in FIGS. 2 and 3. Here, the cardboard 10 does not have to form a cap which surrounds the total surface of the counter electrode 6, but it can also be arranged at the outer surface of the open part of the counter electrode 6, for example by means of an adhesive tape. FIG. 4 shows a measuring cell where the active part is a ring-shaped surface area 9 of the electro-chemical element. In FIG. 5 the arrangement of the electro-chemical element is shown in the molten bath with slag adhering to the active part while the counter electrode is already partly melted off and partly coated by slag.

We claim:

1. A dipping measuring sensor to measure an electrochemical activity of a non-metallic material which forms a liquid layer lying on a molten bath comprising: a solid electrolyte electrochemical element arranged in a holder with a counter electrode, wherein on insertion into the liquid layer a protection layer (10) of non-fireproof material is arranged at the counter electrode (6), and the electrochemical element (1) has no protection layer.

2. The dipping measuring sensor according to claim 1, wherein the protection layer (10) comprises cardboard.

3. The dipping measuring sensor according to claim 1, wherein the protection layer (10) covers the total surface of the counter electrode (6) outside of the holder.

4. The dipping measuring sensor according to claim 1, wherein the electrochemical element projects approximately 9 to 13 mm out of the holder.

5. The dipping measuring sensor according to claim 1, wherein the holder includes an insertion end, a cardboard tube (4) is arranged on the holder, and a measuring head of fire-proof material (3) is arranged at the insertion end, the electrochemical element (1) and the counter electrode (6) are arranged at the front of the measuring head, and the counter electrode (6) at least partly surrounds the electrochemical element (1).

6. The dipping measuring sensor according to claim 1, wherein the counter electrode (6) includes a contact, the electrochemical element (1) includes a contact, and the contacts are led inside the holder and are connected to measurement and evaluation electronics.

7. A measuring cell to measure the electrochemical activity of a material which forms a non-metallic liquid layer lying on a molten bath, comprising:

an electrochemical element (1) arranged in a holder having a fire-proof body (2), said electrochemical element having a small solid-electrolyte tube (7) with an active part, a counter electrode (6) spaced from the electrochemical element (1), the electrochemical element (1) and the counter electrode (6) being adapted to be arranged in the molten bath, with the active part being surrounded by the non-metallic material to be measured and at least one part of the counter electrode having direct contact with the molten bath, the small solid-electrolyte tube (7) includes an insertion end which is coated with an electrically insulating material (8) comprising one of $Al_2O_3$ and MgO, and an area between the insertion end and the fire-proof body (2) is not coated.

8. A measuring cell to measure the electrochemical activity of a material which forms a non-metallic liquid layer lying on a molten bath, comprising:

an electrochemical element (1) arranged in a holder having a fire-proof body (2), said electrochemical element having a small solid-electrolyte tube (7) with an active part, a counter electrode (6) spaced from the electrochemical element, the electrochemical element (1) and the counter electrode (6) being adapted to be arranged in the molten bath, with the active part being surrounded by the non-metallic material to be measured and at least one part of the counter electrode having direct contact with the molten bath, and the active part of the electrochemical element (1) has a ring-shaped surface area (9).

* * * * *